United States Patent
Vorbuchner

(10) Patent No.: US 7,647,649 B2
(45) Date of Patent: Jan. 19, 2010

(54) BODY-WORN ARTICLE FUNCTIONING AS A POSITIONING DEVICE ALLOWING PATIENT POSITIONING RELATIVE TO MEDICAL THERAPY OR EXAMINATION DEVICE

(75) Inventor: Marianne Vorbuchner, Erlangen-Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 857 days.

(21) Appl. No.: 10/927,680

(22) Filed: Aug. 27, 2004

(65) Prior Publication Data

US 2005/0049483 A1    Mar. 3, 2005

(30) Foreign Application Priority Data

Aug. 29, 2003    (DE) .................. 103 40 002

(51) Int. Cl.
*A41D 1/06* (2006.01)

(52) U.S. Cl. .................. 2/238; 600/407; 600/410; 600/414; 250/491.1

(58) Field of Classification Search ............ 600/414, 600/410, 411, 415; 2/455, 456, 88, 106, 2/108, 79; 5/601, 620–624, 630; 128/845, 128/846; 250/491.1
See application file for complete search history.

(56) References Cited

U.S. PATENT DOCUMENTS

| | | | |
|---|---|---|---|
| 5,123,407 A | | 6/1992 | Dewhurst |
| 5,368,030 A | * | 11/1994 | Zinreich et al. .............. 600/414 |
| 5,370,117 A | | 12/1994 | McLaurin, Jr. |
| 5,427,099 A | * | 6/1995 | Adams .................. 600/414 |
| 5,469,847 A | * | 11/1995 | Zinreich et al. ............... 600/414 |
| 5,531,227 A | * | 7/1996 | Schneider ................. 600/425 |
| 5,695,501 A | * | 12/1997 | Carol et al. ................. 606/130 |
| 5,702,406 A | | 12/1997 | Vilsmeier et al. |
| 5,755,746 A | * | 5/1998 | Lifshey et al. .............. 607/50 |
| 5,911,126 A | | 6/1999 | Massen |
| 5,967,980 A | * | 10/1999 | Ferre et al. .................. 600/424 |
| 6,491,699 B1 | * | 12/2002 | Henderson et al. ............ 606/130 |
| 6,567,687 B2 | * | 5/2003 | Front et al. ................. 600/426 |
| 6,611,700 B1 | * | 8/2003 | Vilsmeier et al. ............ 600/407 |
| 6,830,344 B2 | * | 12/2004 | Reho et al. .................. 353/122 |
| 6,966,087 B2 | * | 11/2005 | Robinette ....................... 5/625 |
| 7,127,826 B2 | * | 10/2006 | Russell ......................... 33/758 |
| 2002/0087101 A1 | * | 7/2002 | Barrick et al. ................ 600/587 |
| 2003/0114893 A1 | | 6/2003 | Nathan et al. |
| 2003/0137510 A1 | | 7/2003 | Massen |
| 2005/0261570 A1 | * | 11/2005 | Mate et al. .................. 600/411 |

FOREIGN PATENT DOCUMENTS

| | | |
|---|---|---|
| DE | 33 40 482 | 4/1986 |
| DE | 199 08 903 | 4/2001 |
| WO | WO 02/32328 | 4/2002 |

* cited by examiner

*Primary Examiner*—Brian Casler
*Assistant Examiner*—Parikha S Mehta
(74) *Attorney, Agent, or Firm*—Schiff Hardin LLP

(57) ABSTRACT

A positioning device is applied in a reproducible manner to a patient, allows indication of the position of an anatomical area of the patient, allows the patient to be positioned in a reproducible manner in relation to an examination area of a medical examination device and a therapy area of a therapy device, and includes an antenna arrangement for the examination with a magnetic resonance device. In one embodiment, the positioning device also includes an arrangement for immobilizing the patient.

18 Claims, 2 Drawing Sheets

BODY-WORN ARTICLE FUNCTIONING AS A POSITIONING DEVICE ALLOWING PATIENT POSITIONING RELATIVE TO MEDICAL THERAPY OR EXAMINATION DEVICE

BACKGROUND OF THE INVENTION

The present invention relates to a positioning device for positioning a patient in relation to a medical examination or therapy device. The device is configured for multiple use by a plurality of patients and comprises means for indicating the position of an anatomical area of one of the patients in relation to the positioning device and means for the reproducible positioning of the patient in relation to an examination or therapy area of the medical examination or therapy device.

The positioning of a patient to be examined or treated correctively in relation to an examination or therapy device is essential for the effectiveness of a treatment. The positioning requires a correspondingly high level of accuracy. When carrying out complex treatments, for which examination and therapy devices are deployed in an alternating manner, reproducible positioning of the patient is of crucial importance. One example of such a complex treatment is radiotherapy, in which, on the one hand, examinations are carried out using medical imaging devices for diagnosis purposes and, on the other hand, therapy takes place with radiotherapy devices. Generally the success of the treatment is finally monitored again using a medical imaging device, for example a magnetic resonance device, which is known as a MR device, or a computer tomography device, which is known as a CT device.

With such complex treatments, information obtained during the examination, such as the position of a tumor in the body, is required for therapy, in order, for example, to draw up a radiation plan. To allow the transfer of such information from the examination device to the therapy device, markings are generally painted on the body of the patient and located in relation to the different examination or therapy devices. Such markings can be lost over time, for example if the patient is cleaned with alcohol. But in the case of radiotherapy, radiation treatment is divided into a plurality of radiation sessions. For example, between 20 and 30 sessions are normally required for prostate radiation. In addition, several control examinations are carried out, for example, using CT or MR devices. The tumor radiation is closely followed by a number of examinations to monitor the success of the radiation. The patient has to be repositioned for each of these examinations or radiation sessions. This is very time-intensive and there is a risk of incorrect positioning. Poor positioning results in an avoidable, additional radiation load due to inaccurate radiation and additional CT control examinations.

Alternatives to the above-mentioned painting of markings on the patient are, for example, fitted devices produced individually for each patient and requiring a great deal of time and effort or plaster casts for children. For example, DE 33 40 482 C2 discloses a device for producing a transparent and radiation-permeable mask for applying the marking required for the accurate radiation of human body parts. The individually tailored, patient-specific mask is positioned and fixed in the correct place on the patient. Characteristic lines are used to identify both the place at which radiotherapy is to be carried out and also the three-dimensional position of the body part in relation to the device.

Additional devices are, for example, known from U.S. Pat. No. 5,370,117 and U.S. Pat. No. 5,702,406, which claims priority from DE 44 32 891 A1. For example, U.S. Pat. No. 5,702,406 discloses a device for non-invasive steriotactic immobilization in a reproducible position. It comprises a mask made of a number of elements, which is tailored individually to the anatomical contours of a patient and is connected via a connecting device to a reference system, in particular a head ring.

The use of markers is known from DE 199 08 903 C2, WO 02/32328 A2 and US 2003/0137510 A1, which claims priority from DE 10025 922 A1 and the use of a template from U.S. Pat. No. 5,911,126, which claims priority from EP 0 760 622 B1.

A system for automatic identification of the shape of a patient and for instrument position determination is known from US 2002/0087101 A1. The external shape of a patient is thereby determined using a first set of curve sensors and aligned with volumetric image data from CT or MR devices. The position of an instrument is established using a second set of curve sensors in relation to the first set and, therefore, in relation to the image data set.

A device for functional electrical stimulation of a body part is known from US 2003/0114893 A1. Accurate, simple and repeatable positioning of the device in relation to activation points of muscles of the body part is achieved using a location system, which comprises both means for allowing rotation-related location and also means which allow longitudinal location of the device.

A device for aligning the hip, e.g. during sleep, is known from U.S. Pat. No. 5,123,407.

SUMMARY OF THE INVENTION

The object of the invention is to facilitate the positioning of a patient in relation to a medical examination or therapy device.

According to the invention, this object is achieved by a positioning device of the type mentioned above, whereby the positioning device also comprises means for reproducible application of the positioning device to a patient in relation to the anatomy of the patient and an antenna arrangement for an examination with a magnetic resonance device.

The positioning device according to the invention is simple to operate and can be deployed in a time-saving and economical manner. Areas of application for the positioning device include, for example, MR, CT and ultrasound examinations as well as radiotherapy. The positioning device is preferably configured for economical multiple use by one or a plurality of patients.

The position of an anatomical area of interest in relation to the anatomy of the patient is, for example, determined using a medical imaging examination device. It can be located using the means for indicating the position of the anatomical area in relation to the positioning device.

As the positioning device can be applied by the patient reproducibly in an identical manner, it is possible to position the anatomical area specifically at one point in the space. This is achieved using the means for reproducible positioning, which make it possible, for example, to align the positioning device so that the anatomical area is in the respective area of coverage of the medical device. A prerequisite for this is that the positioning device can be applied with the required accuracy in an exactly reproducible manner in relation to the anatomy even when applied more than once.

One main advantage of the positioning device is to facilitate reproducibility of the position of the patient in the examination or therapy device. It therefore results in more accurate positioning of the anatomical area, which is of interest for the examination or therapy. For example, the already-known anatomical position of a tumor can be positioned accurately and radiated effectively according to a radiation plan using the positioning device.

Another advantage of the positioning device results from its use in CT and MR examinations. If these are carried out in an identical anatomical position, this facilitates the calculation of the radiation dosage by means of CT/MR image fusion reconstruction, with which the radiation plan is based on the MR images.

One additional advantage is the facilitated execution of control examinations directly after radiation when using the positioning device.

Another advantage of the positioning device is that it eliminates the need for supporting CT examinations during positioning and radiation planning. This makes it possible for the positioning device to be used as a reference point for geometric radiation planning. The radiation load due to the necessary CT examinations is correspondingly eliminated.

Means for reproducible application can also preferably be used to indicate the position of an anatomical area or for reproducible positioning. In the same way, means for indicating the position of an anatomical area can be used for reproducible positioning. Any kind of multiple use of the means is therefore conceivable.

The positioning device can be deployed in a method for positioning a patient in a medical examination or therapy device. The positioning device is applied to a patient and the means for reproducible application are used to achieve a reproducible location of the positioning device in relation to the anatomy of the patient and the position of the patient in the medical examination or therapy device is aligned using the positioning device. Position alignment is effected in that the anatomical area is assigned as accurately as possible to the examination area.

The advantage of using the positioning device in such a method is also the accurate, fast and simple positioning of the patient. It therefore also results in an improved accuracy during the radiation of tumors.

In one advantageous embodiment, the positioning device comprises a material, which is mapped by the examination device. This has the advantage that information obtained during the examination can be located spatially in direct relation to the positioning device.

In particular advantageous embodiments, the positioning device is an article of clothing selected from a group consisting of a pair of trousers, a shirt and a wrap. Positioning devices thus configured have the advantage that they can easily be tailored to a body shape. The positioning device is preferably available in a plurality of sizes, so that it can be tailored to different anatomical sizes.

In one advantageous embodiment, the positioning device has a grid on its outer surface or side when applied. Such a grid has the advantage that an anatomical feature, such as a hip-bone or navel, can be assigned a unique position in the grid. The grid can also be used to determine additional information, such as a reference to the position of an area of interest or a favorable radiation direction.

In one particularly advantageous embodiment of the positioning device, the means for reproducible application and/or the means for indicating the position of an anatomical area and/or the means for reproducible positioning comprise at least one marker. Such a marker can be located specifically on the positioning device, for example to provide a reference to the anatomical area of interest. Such a marker can thereby also be used as a means for reproducible application and/or means for indicating the position of an anatomical area and/or means for reproducible positioning.

The marker preferably comprises a material, which is mapped by the examination device, for example proton-rich materials for MR examinations. In this way, the reference by the marker to the anatomical area can also be achieved by means of an MR or CT image. Alternatively, the marker comprises attachment devices, which, in particular, allow the marker to be adhered to the adhesion points on the positioning device. The adhesive surfaces are preferably configured so that the markers can be easily removed.

In another embodiment of the positioning device, the means for reproducible application comprises a recess in the positioning device. This has the advantage that, for example, an anatomical feature, such as a hip-bone, can be used for reproducible application of the positioning device. For this purpose, the recess is located centrally, for example over the anatomical feature.

In another advantageous embodiment of the positioning device, the means for reproducible positioning comprise a target cross for a positioning light on the examination or therapy device. In this way, for example, the standard positioning light on the CT or MR devices can be used to position the patient in the examination or therapy device.

An antenna arrangement present according to the invention acts as a high-frequency MR antenna arrangement in proximity to the organ to provide optimum resolution and good image quality. An additional advantage is the reliable and precisely reproducible position of the antenna arrangement in relation to the anatomy. In one advantageous embodiment, the positioning device comprises an antenna arrangement that can be positioned in a reproducible manner for examinations with a magnetic resonance device. The antenna arrangement can preferably be located in a reproducible manner on the positioning device. This can be achieved, for example, using a pocket in the positioning device, and the antenna arrangement is inserted into the pocket. In the event that it is not required, for example during a CT examination, the antenna is removed from the pocket.

Other advantages and features of the invention will be readily apparent from the following description, the claims and drawings.

A plurality of exemplary embodiments of the invention is described below with reference to FIGS. 1 and 2.

DESCRIPTION OF THE PREFERRED EMBODIMENTS

Figure 1:
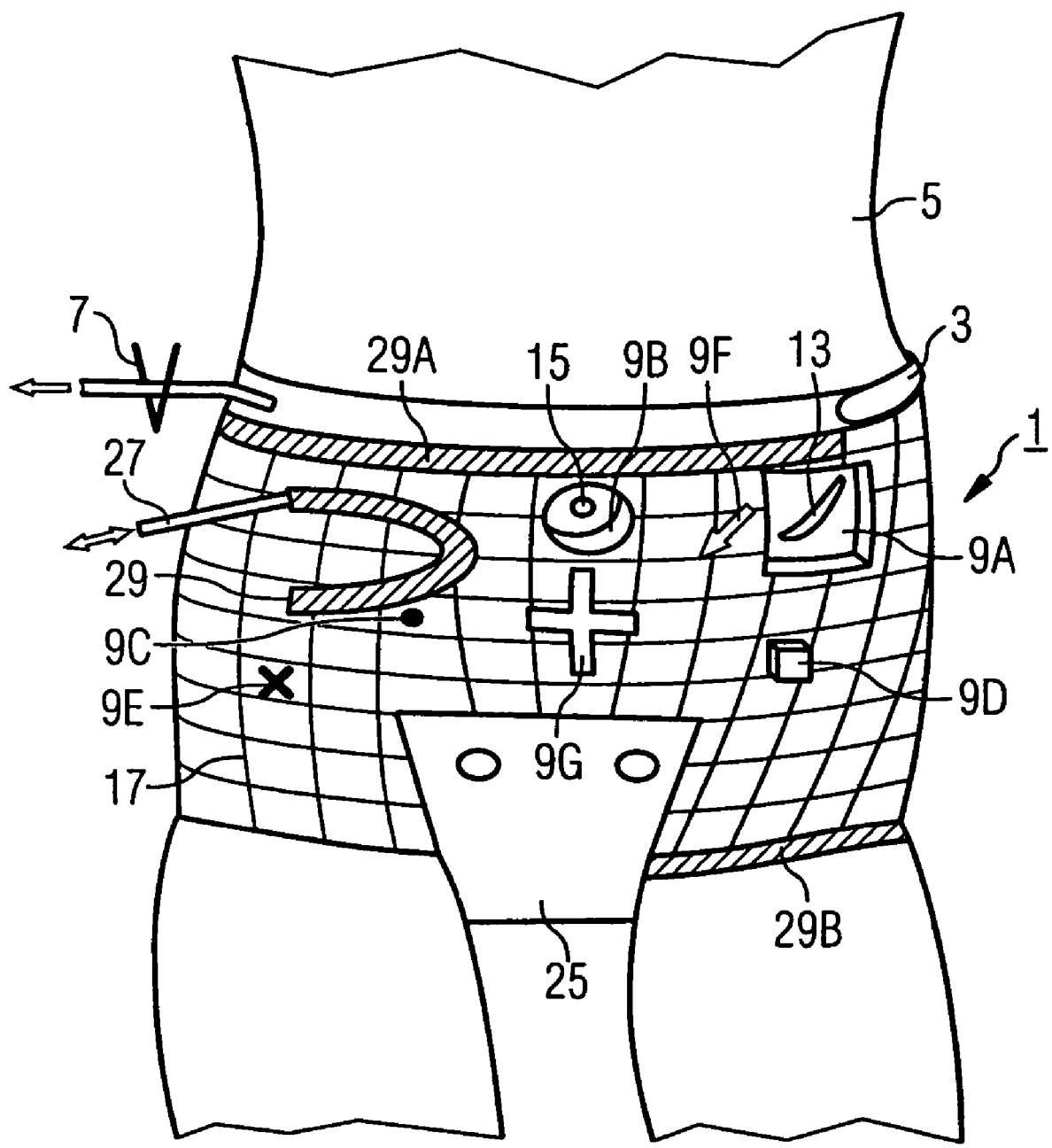
FIG. 1 shows an example of a multifunctional positioning unit.

FIG. 1 shows an example of a multifunctional positioning unit 1 according to the invention. It is designed, for example, for the identification and treatment of carcinoma of the prostate, and it can be deployed in the various phases of the treatment (MR examinations, CT examinations and radiotherapy). For this purpose, it is put on like a pair of trousers or shorts for every examination or radiation session. A Velcro fastening 3 allows the size of the positioning unit 1 to be adjusted for a patient 5. The positioning unit 1 comprises a short or brief style, twin-walled wrap with an inner space, into which a filler material is inserted. An evacuation unit can be operated via a valve 7 to evacuate the twin-walled positioning unit and the filler material allows the positioning unit 1 to be adjusted correctly to the body of the patient 5. The freedom of movement of the patient is also advantageously restricted by the filler material, so that the patient remains immobilized and stabilized in position. Such immobilization of the patient 5 is particularly advantageous when the patient 5 is undergoing radiotherapy. It can also be achieved, for example, by closing the Velcro fastening 3 tightly, thereby restricting the capacity for movement of the patient 5.

While the positioning unit 1 is being applied, markers, for example recesses 9A and 9B, are arranged in a reproducible position, e.g. on anatomical features of the patient 5, for example the iliac crest 13, navel 15 or an appendix scar. Alternatively, the positioning unit 1 can comprise transparent areas or markings 9C, which are positioned above the anatomical features.

The positioning unit 1 also has a grid 17, which divides out the surface of the positioning unit 1. Special markers 9D, which have, for example, a high proton ratio for strong magnetic resonance signals, can be located precisely on the positioning unit 1 using the grid 17. Alternatively, crosses 9E or other characters, for example arrows 9F, can be painted on the positioning unit 1. The grid preferably has a coordinates system.

The positioning unit 1 can also comprise a gradually tapering flap 25, which can be closed, for example, during location of the prostate. If the positioning unit 1 is configured as a shirt, the flap 25 can be configured, for example, in the form of two holders. The flap 25 or holders maintain the unique position of the positioning unit 1. An alternative embodiment of the positioning unit 1 has no flap 25 and is applied using the Velcro fastening 3 to any position as a wrap on the patient 5.

The positioning unit 1 can be positioned using the markings 9A-9G, on the one hand, in a precisely reproducible position in relation to the anatomy of the patient 5 and, on the other hand, it can define the position of the anatomical area in relation to itself using the markings 9A-9G.

For example, a CT or MR image obtained with the positioning unit 1 is automatically spatially related to the positioning unit 1. The information obtained from the MR examination on the position of the anatomical area can be recorded optically on the positioning unit 1 using the means for indicating the position of an anatomical area. The different markers/markings 9A-9G can, for example, serve as reference points or define a direction.

The means for reproducible positioning of the patient can be used to position the anatomical area in the examination or therapy area of a medical examination or therapy device. For this, the positioning unit 1, for example, comprises a cross-hair 9G, which is used as the target for an optical cross-hair on an examination or therapy device. Future or past markers can also assist with reproducible positioning. Some of the markers used correspond to the markings generally painted on the body of a patient.

The materials of the positioning unit 1 are preferably transparent to radiation, non-electrical and non-magnetic, so that they can be used in x-ray, CT and MR devices. Coils can preferably be attached to the positioning unit 1. For example, a coil 27 can be inserted in a pocket 29. Such coils are advantageously arranged by the position of their pocket 29, 29A, 29B in relation to the area of the patient 5 to be examined. Alternatively, the coils can be attached using Velcro strips. They preferably run in a horizontal and vertical direction and as close as possible around the organ.

The positioning unit with the coil 27 allows non-invasive examination of the patient 5, during which, for example, an anatomical area can be detected and located. For example, an area to undergo radiotherapy can be identified. This is then moved into the examination or therapy area of the medical examination or therapy device using the positioning device.

Figure 2:
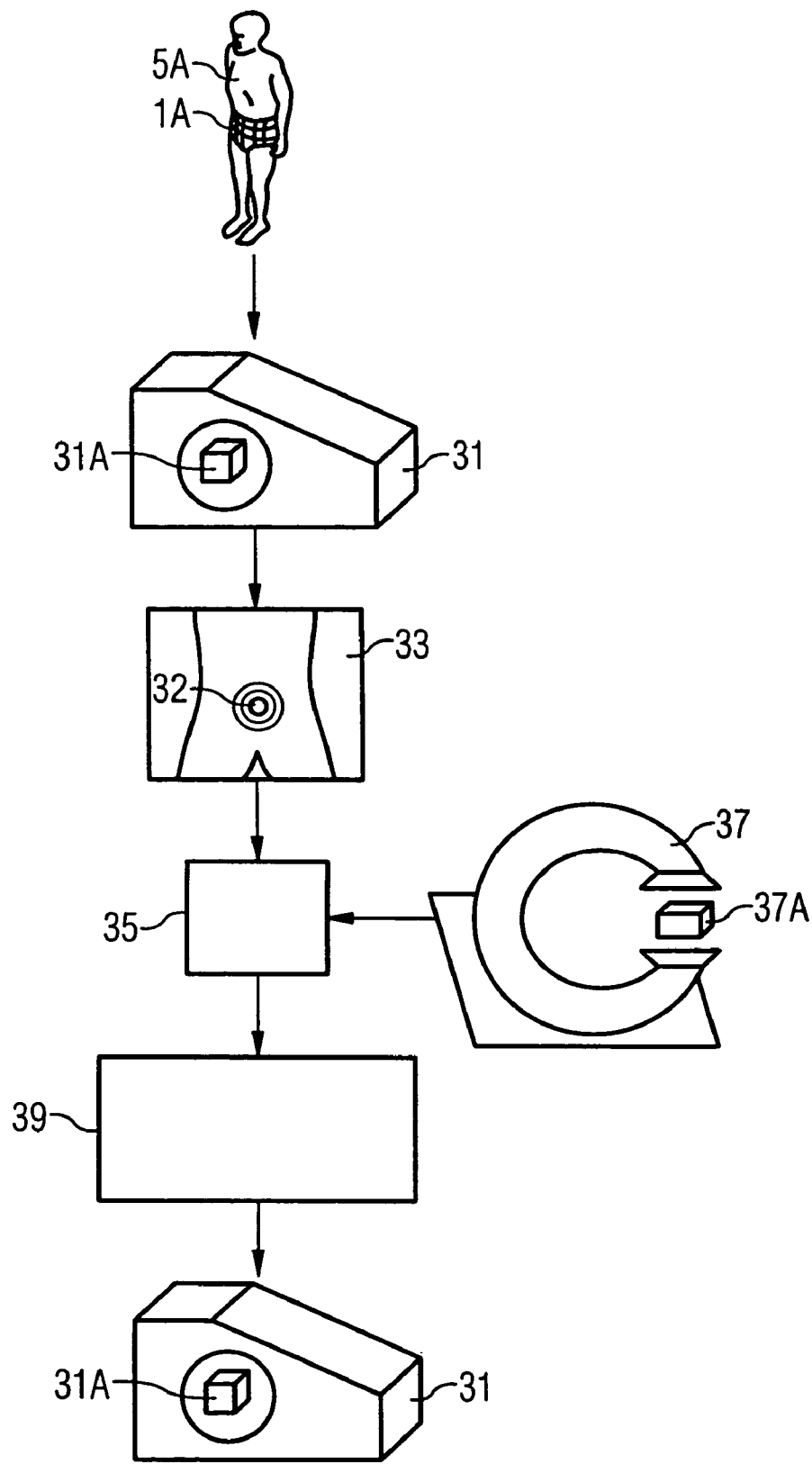
FIG. 2 shows a flow diagram of the exemplary use of a positioning unit according to the invention.

FIG. 2 describes the sequence for the use of a positioning unit 1A according to the invention. A patient 5A is, for example, examined because of a suspected carcinoma using an imaging examination device, for example either a MR or CT device. For this purpose, the positioning unit 1A is adjusted for the patient 5A, so that it can be applied in a reproducible manner, for example, its position in relation to the anatomy of the patient 5A is recorded using markers.

The patient is preferably positioned in a reproducible manner in a magnetic resonance device 31 with an examination area 31A using additional or the same markers or using characters marked on the patient 5A and an MR examination is carried out. The position of the positioning unit 1A in relation to the anatomy can be identified from the MR images obtained.

The carcinoma is located by means of an analysis of the MR examination, for example, by analyzing ratios of specific metabolites. The coordinates of the anatomical area of interest 32, provided here by the carcinoma, are determined in relation to the positioning unit 1A using a metabolite image 33. A radiation plan 35 is drawn up on this basis. Alternatively, additional information from an examination using a CT device 37 with an examination area 37B can be included when drawing up the radiation plan 35.

The radiation plan 35 is used to subject the patient 5A to radiotherapy using a therapy device 39. the positioning unit 1A is applied to the patient 5A again for this purpose. The radiation plan 35 and, in particular, the CT or the MR images are used to locate additional markers on the positioning unit 1A to allow alignment of the patient 5A in relation to the radiation.

Finally, the MR examinations 31 or the CT examinations 37 are carried out to monitor the progress or success of the treatment. The markers applied facilitate the positioning of the patient, so that the anatomical area is located in a therapy area of the therapy device.

Although various minor modifications may be suggested by those versed in the art, it should be understood that I wish to embody within the scope of the patent granted hereon all such modifications as reasonably and properly come within the scope of my contribution to the art.

I claim:

1. A single unitary positioning device comprising:
   a body-worn article that is configured to be worn by and removed from each of a plurality of patients and that is differently configurable for multiple use by each of said plurality of patients;
   said body-worn article including an anatomical indicator, permanently built into said body-worn article, that, for each patient, among the plurality of patients, wearing the body-worn article indicates the position of an anatomical area of that patient and thereby causes the body-worn article to always be identically positioned on that patient solely by that patient donning said body-worn article;
   said body-worn article having a visually perceivable spatial relation indicator thereon;
   said body-worn article further having a position indicator that is selectively positionable on said body-worn article with a reproducible spatial relation to said anatomical indicator, by means of said spatial relation indicator, to cause said body-worn article to be positioned on any of the plurality of patients currently wearing the body-worn article with said anatomical area in reproducible relation to an area selected from the group consisting of an examination area of a medical device and a therapy area of a medical therapy device; and said body-worn article having a receptacle containing an antenna arrangement configured for an examination with a magnetic resonance device.

2. A positioning device according to claim 1, wherein the body-worn article comprises a material which is detectable by the examination device.

3. A positioning device according to claim 2, wherein the body-worn article is a pair of shorts, an element of clothing selected from a group consisting of trousers, a shirt and a wrap.

4. A positioning device according to claim 1, wherein said spatial relation indicator is a grid on an outer surface of the body-worn article.

5. A positioning device according to claim 1, wherein the positioning device comprises a writing on an outer surface of the body-worn article and wherein the positioning device is configured to allow said writing to be applied after the body-worn article is donned by a patient.

6. A positioning device according to claim 1, wherein one of the anatomical indication and the position indicator comprises at least one marker.

7. A positioning device according to claim 6, wherein the marker comprises a material which is detectable by the examining device.

8. A positioning device according to claim 7, wherein the marker comprises an attachment device.

9. A positioning device according to claim 8, wherein the attachment device comprises an adhesive surface configured to attach the marker to an adhesion point on the body-worn article.

10. A positioning device according to claim 6, wherein the marker comprises an attachment device.

11. A positioning device according to claim 10, wherein the attachment device comprises an adhesive surface configured to attach the marker to an adhesion point on the body-worn article.

12. A positioning device according to claim 1, wherein the position indicator comprises a target cross for a positioning light beam of one of the examination and therapy device.

13. A positioning device according to claim 1, wherein the antenna arrangement is configured to be inserted into a pocket of the body-worn article.

14. A positioning device according to claim 1, wherein the body-worn article and all of said indicators are comprise non-magnetic and non-electrical materials.

15. A positioning device according to claim 1, wherein the positioning device also includes a component that is operable to immobilize the patient.

16. A positioning device according to claim 15, wherein said component that is operable to immobilize the patient comprises a volume incorporated into the body-worn article that is evacuable and is filled with a filler material of an adjustable shape.

17. A positioning device according to claim 1, wherein the body-worn article is an article of clothing selected from a group consisting of a pair of trousers, a pair of shorts, a shirt and a wrap.

18. A position positioning device as claimed in claim 1 wherein said anatomical indicator is an opening in said body-worn article configured for placement over an anatomical landmark of each patient in said plurality of patients, to allow the anatomical landmark to be visually perceivable through the opening.

* * * * *